US009566453B2

(12) United States Patent
Tachibana (10) Patent No.: US 9,566,453 B2
(45) Date of Patent: Feb. 14, 2017

(54) CHARGED PARTICLE BEAM IRRADIATION APPARATUS

(71) Applicant: Sumitomo Heavy Industries, Ltd., Tokyo (JP)

(72) Inventor: Masanori Tachibana, Ehime (JP)

(73) Assignee: Sumitomo Heavy Industries, Ltd., Tokyo (JP)

( * ) Notice: Subject to any disclaimer, the term of this patent is extended or adjusted under 35 U.S.C. 154(b) by 0 days.

(21) Appl. No.: 15/085,771

(22) Filed: Mar. 30, 2016

(65) Prior Publication Data
US 2016/0279446 A1 Sep. 29, 2016

Related U.S. Application Data

(63) Continuation of application No. PCT/JP2014/070070, filed on Jul. 30, 2014.

(30) Foreign Application Priority Data

Oct. 15, 2013 (JP) .................................. 2013-214681

(51) Int. Cl.
*A61N 5/00* (2006.01)
*A61N 5/10* (2006.01)

(52) U.S. Cl.
CPC ..... *A61N 5/1081* (2013.01); *A61N 2005/1087* (2013.01)

(58) Field of Classification Search
CPC .. A61N 5/1077; A61N 5/1078; A61N 5/1079; A61N 5/1081; A61N 5/1087
(Continued)

(56) References Cited

U.S. PATENT DOCUMENTS 6,462,490 B1* 10/2002 Matsuda .................. H05H 7/02
250/492.3
2005/0231138 A1* 10/2005 Nakanishi ................ G21K 5/04
315/500
(Continued)

FOREIGN PATENT DOCUMENTS

JP 2011-156340 A 8/2011
JP 2011-239841 A 12/2011
(Continued)

OTHER PUBLICATIONS

International Search Report issued in Application No. PCT/JP2014/070070, mailed Oct. 7, 2014.

*Primary Examiner* — Jason McCormack
(74) *Attorney, Agent, or Firm* — Michael Best & Friedrich LLP (57) ABSTRACT

A charged particle beam irradiation apparatus includes: an accelerator which accelerates charged particles and emits a charged particle beam; an irradiation unit which irradiates an irradiation target with the charged particle beam; a transport line which transports the charged particle beam emitted from the accelerator, to the irradiation unit; an energy adjustment unit which is provided at the transport line and adjusts energy of the charged particle beam; a plurality of electromagnets provided further toward the downstream side than the energy adjustment unit in the transport line; an electromagnet power source provided to correspond to each of the electromagnets; and a control unit which controls a parameter of the electromagnet according to the energy of the charged particle beam, wherein the electromagnet power source has a storage unit which stores the parameter of the electromagnet for each layer which is irradiated with the charged particle beam, in the irradiation target.

4 Claims, 5 Drawing Sheets

(58) Field of Classification Search
USPC .......................................... 250/492.1, 492.3
See application file for complete search history.

(56) References Cited

U.S. PATENT DOCUMENTS

| | | | | |
|---|---|---|---|---|
| 2009/0003524 A1* | 1/2009 | Pu | ............................ | A61N 5/10 |
| | | | | 378/65 |
| 2012/0056098 A1* | 3/2012 | Harada | ................ | A61N 5/1042 |
| | | | | 250/396 R |
| 2012/0228521 A1* | 9/2012 | Honda | ................ | A61N 5/1043 |
| | | | | 250/492.3 |
| 2014/0319383 A1 | 10/2014 | Yajima | | |

FOREIGN PATENT DOCUMENTS

| | | | |
|---|---|---|---|
| JP | 2013-153993 A | 8/2013 | |
| JP | 2013-198579 A | 10/2013 | |
| WO | WO-2013/108534 A1 | 7/2013 | |
| WO | WO-2013/140856 A1 | 9/2013 | |

* cited by examiner

CHARGED PARTICLE BEAM IRRADIATION APPARATUS

RELATED APPLICATIONS

Priority is claimed to Japanese Patent Application No. 2013-214681, filed Oct. 15, 2013, and International Patent Application No. PCT/JP2014/070070, the entire content of each of which is incorporated herein by reference.

BACKGROUND

Technical Field

A certain embodiment of the invention relates to a charged particle beam irradiation apparatus for irradiating an irradiation target with a charged particle beam.

Description of Related Art

As a charged particle beam irradiation apparatus which is used in radiation therapy, a charged particle beam irradiation apparatus disclosed in the related art is known. In the related art, the charged particle beam irradiation apparatus is described in which a parameter corresponding to each of a plurality of spots in an irradiation target is accumulated, a parameter corresponding to a predetermined spot among the parameters is output to an excitation unit as one unified transmission signal, and a charged particle beam is sequentially incident on a predetermined spot, based on the parameter. In this charged particle beam irradiation apparatus, if the irradiation of all the spots of a certain layer with the charged particle beam is completed, the energy of the charged particle beam is changed and the irradiation of the spots of the next layer with a charged particle beam is performed.

SUMMARY

According to an embodiment of the present invention, there is provided a charged particle beam irradiation apparatus including: an accelerator which accelerates charged particles and emits a charged particle beam; an irradiation unit which irradiates an irradiation target with the charged particle beam; a transport line which transports the charged particle beam emitted from the accelerator, to the irradiation unit; an energy adjustment unit which is provided at the transport line and adjusts energy of the charged particle beam; a plurality of electromagnets provided further toward the downstream side than the energy adjustment unit in the transport line; an electromagnet power source provided to correspond to each of the plurality of electromagnets; and a control unit which controls a parameter of the electromagnet according to the energy of the charged particle beam, wherein the electromagnet power source has a storage unit which stores the parameter of the electromagnet for each layer which is irradiated with the charged particle beam, in the irradiation target, and the control unit transmits a signal relating to switching of a layer to the electromagnet power source.

DETAILED DESCRIPTION

In a charged particle beam irradiation apparatus, it is desired to shorten an irradiation time in order to reduce a burden on a patient during treatment. However, in the charged particle beam irradiation apparatus of the related art described above, each time the layer to be irradiated is switched, it is necessary to transmit parameters corresponding to a plurality of spots of a layer after switching, and thus time is required for switching a layer.

Therefore, in this technical field, it is desirable to shorten an irradiation time by shortening a layer switching time.

In the charged particle beam irradiation apparatus according to an embodiment of the present invention, the electromagnet power source has the storage unit which stores the parameter of the electromagnet for each layer in the irradiation target. Further, the control unit transmits a signal relating to switching of a layer to the electromagnet power source. For this reason, in the electromagnet power source, it is possible to set the parameter of the electromagnet of one layer stored in its own storage unit, based on the signal relating to switching of a layer transmitted from the control unit. In this manner, the parameter of the electromagnet for each layer is kept and stored in the storage unit of the electromagnet power source, whereby at the time of layer switching, it is not necessary to transmit the parameter itself for each layer from the control unit to the electromagnet power source and it is enough if a signal to simply give notice of a timing of switching is transmitted. Accordingly, it is possible to shorten an irradiation time by shortening a layer switching time.

Further, in the charged particle beam irradiation apparatus described above, the control unit may transmit a signal to identify a layer, as the signal relating to switching of a layer, and the electromagnet power source may set a parameter of one layer among the parameters of the electromagnet stored for each layer, according to the signal to identify a layer received from the control unit. The signal to identify a layer is transmitted by the control unit, whereby the electromagnet power source can uniquely identify the parameter of a layer which is set after switching. Accordingly, layer switching processing becomes easy.

Further, the charged particle beam irradiation apparatus described above may further include a rotary gantry rotatable around the irradiation target, wherein the irradiation unit may be mounted on the rotary gantry and the energy adjustment unit may be provided between the accelerator and the rotary gantry. The irradiation unit is mounted on the rotary gantry, whereby the irradiation target can be irradiated with the charged particle beam from multiple directions. In this way, it is possible to more effectively perform the irradiation of the irradiation target with the charged particle beam. Further, the energy adjustment unit is provided between the accelerator and the rotary gantry, whereby it is possible to reliably adjust the energy of the charged particle beam emitted from the accelerator, before the irradiation of the irradiation target.

Further, in the charged particle beam irradiation apparatus described above, the energy adjustment unit may be provided at a position closer to the accelerator than the rotary gantry. The energy adjustment unit is for receiving the charged particle beam and lowering the energy of the charged particle beam and is for emitting a gamma beam, a neutron beam, or the like by being highly activated. Therefore, in a case where the energy adjustment unit is disposed close to the rotary gantry side (that is, the irradiation target side), there is a concern that a radiation dose in a configuration pertaining to irradiation on the irradiation target side may increase. In this regard, the energy adjustment unit is provided on the accelerator side, thereby performing the adjustment of energy at a position sufficiently spaced apart from the irradiation target, whereby an increase in a radiation dose in a configuration pertaining to irradiation on the irradiation target side can be prevented.

According to an embodiment of the present invention, it is possible to shorten an irradiation time by shortening a layer switching time.

Hereinafter, an embodiment of the present invention will be described in detail with reference to the accompanying drawings. In addition, the words "upstream" and "downstream" respectively mean upstream (the accelerator side) and downstream (the patient side) of a charged particle beam which is emitted.

Figure 1:
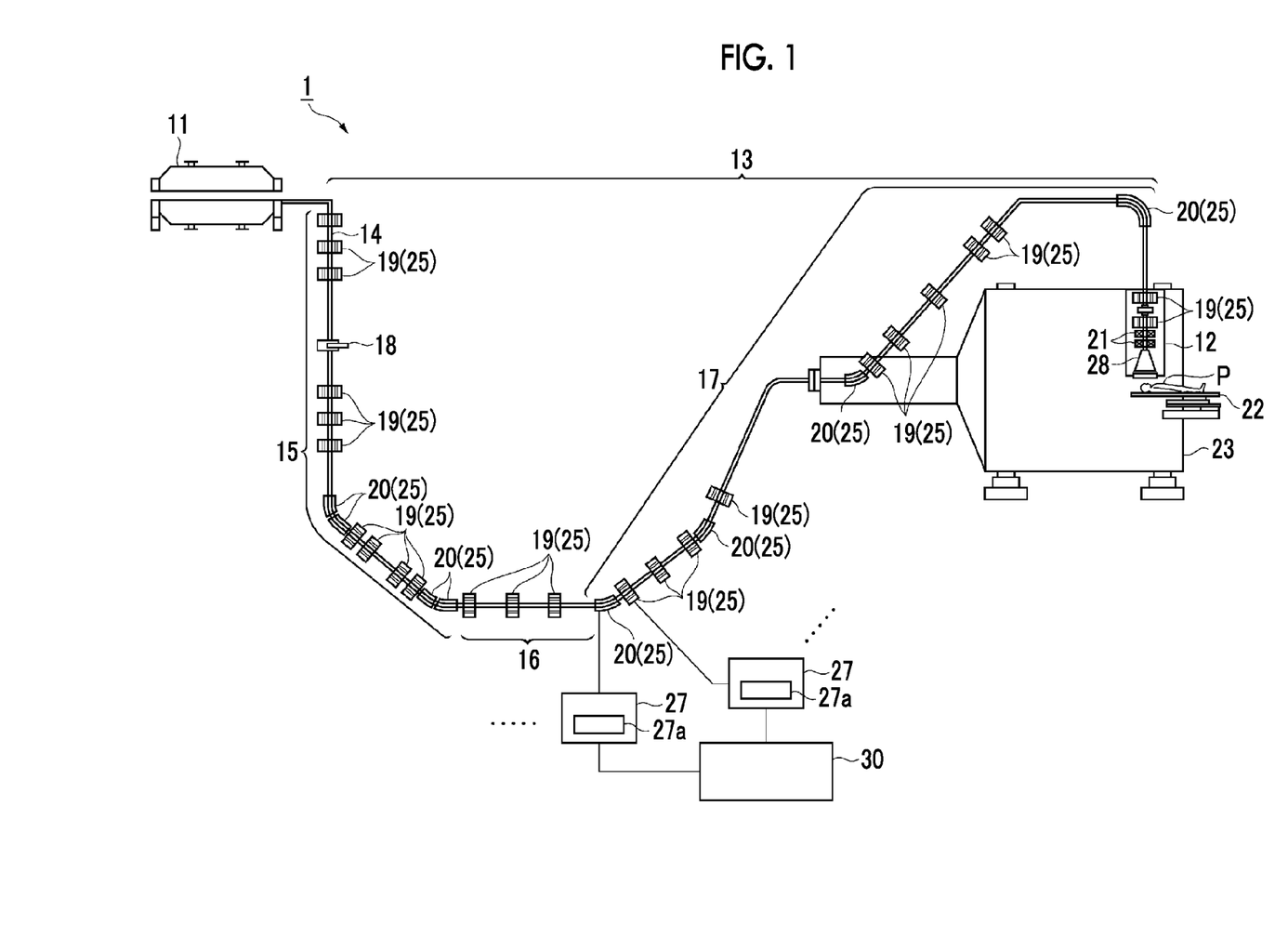
FIG. 1 is a schematic diagram showing a charged particle beam irradiation apparatus according to an embodiment of the present invention.

As shown in FIG. 1, a charged particle beam irradiation apparatus 1 is an apparatus which is used in cancer treatment or the like by radiation therapy, and is provided with: an accelerator 11 which accelerates charged particles and emits a charged particle beam; an irradiation nozzle 12 (an irradiation unit) which irradiates an irradiation target with the charged particle beam; a beam transport line 13 (a transport line) which transports the charged particle beam emitted from the accelerator 11, to the irradiation nozzle 12; a degrader (an energy adjustment unit) 18 which is provided at the beam transport line 13 and adjusts the range of the charged particle beam by lowering the energy of the charged particle beam; a plurality of electromagnets 25 provided at the beam transport line 13; an electromagnet power source 27 provided to correspond to each of the plurality of electromagnets 25; and a control unit 30 which controls the whole of the charged particle beam irradiation apparatus 1. In this embodiment, as the accelerator 11, a cyclotron is adopted. However, there is no limitation thereto, and other generation sources which generate a charged particle beam, for example, a synchrotron, a synchrocyclotron, a linac, or the like is also acceptable.

In the charged particle beam irradiation apparatus 1, the irradiation of the charged particle beam emitted from the accelerator 11 is performed with respect to a tumor (the irradiation target) of a patient P on a treatment table 22. The charged particle beam is a beam obtained by accelerating particles with an electric charge at high speed, and there is, for example, a proton beam, a heavy particle (heavy ion) beam, or the like. The charged particle beam irradiation apparatus 1 according to this embodiment is for performing the irradiation of the charged particle beam by a so-called scanning method, and divides (slices) the irradiation target in a depth direction and performs the irradiation of the charged particle beam with respect to an irradiation range on a layer for each slice plane (layer) (refer to, for example, FIG. 5).

In addition, as an irradiation method by the scanning method, there is, for example, spot-type scanning irradiation and raster-type scanning irradiation. The spot-type scanning irradiation is a method in which if irradiation to one spot which is an irradiation range is completed, beam (charged particle beam) irradiation is temporarily stopped and after preparation of irradiation to the next spot is finished, the irradiation to the next spot is performed. In contrast, the raster-type scanning irradiation is a method in which beam irradiation is continuously performed with respect to an irradiation range of the same layer without stopping irradiation on the way. In this manner, in the raster-type scanning irradiation, beam irradiation is continuously performed with respect to an irradiation range of the same layer, and therefore, unlike the spot-type scanning irradiation, the irradiation range is not composed of a plurality of spots. In the following, an example in which irradiation is performed by the spot-type scanning irradiation will be described, and the irradiation range on the same layer will be described as being composed of a plurality of spots. However, there is no limitation thereto, and in a case where irradiation is performed by the raster-type scanning irradiation, the irradiation range may not be composed of spots, as described above.

The irradiation nozzle 12 is mounted on the inside of a rotary gantry 23 which can rotate 360 degrees around the treatment table 22, and is made to be movable to an arbitrary rotational position by the rotary gantry 23. A convergence electromagnet 19 (the details thereof will be described later), a scanning electromagnet 21, and a vacuum duct 28 are included in the irradiation nozzle 12. The scanning electromagnet 21 is provided in the irradiation nozzle 12. The scanning electromagnet 21 has an X-direction scanning electromagnet for performing scanning with the charged particle beam in an X-direction in a plane intersecting an irradiation direction of the charged particle beam, and a Y-direction scanning electromagnet for performing scanning with the charged particle beam in a Y-direction intersecting the X-direction in the plane intersecting the irradiation direction of the charged particle beam. Further, the charged particle beam for scanning by the scanning electromagnet 21 is deflected in the X-direction and/or the Y-direction, and therefore, the vacuum duct 28 further on the downstream side than the scanning electromagnet is enlarged in diameter as it goes toward the downstream side.

The beam transport line 13 has a vacuum duct 14 through which the charged particle beam passes. The inside of the vacuum duct 14 is maintained in a vacuum state, and thus the charged particles configuring the charged particle beam which is being transported are prevented from being scattered by air or the like.

Further, the beam transport line 13 has: an energy selection system (ESS) 15 which selectively extracts a charged particle beam having an energy width narrower than a predetermined energy width from the charged particle beam emitted from the accelerator 11 and having a predetermined energy width; a beam transport system (BTS) 16 which transports the charged particle beam having an energy width selected by the ESS 15, in a state where energy is maintained; and a gantry transport system (GTS) 17 which transports the charged particle beam toward the rotary gantry 23 from the BTS 16.

The degrader 18 lowers the energy of the charged particle beam which passes therethrough, thereby adjusting the range of the charged particle beam. The depth from the body surface of a patient to a tumor that is an irradiation target is different for each patient, and therefore, when irradiating the patient with the charged particle beam, it is necessary to adjust the range that is an arrival depth of the charged particle beam. The degrader 18 adjusts the energy of the charged particle beam emitted from the accelerator 11 at a constant energy, thereby adjusting the energy of the charged particle beam such that the charged particle beam appropriately reaches the irradiation target which is at a predetermined depth in the body of the patient. Such energy adjustment of the charged particle beam by the degrader 18 is performed for each layer obtained by slicing the irradiation target.

The electromagnet 25 is provided in a plurality at the beam transport line 13 and performs the adjustment of the charged particle beam such that it is possible to transport the charged particle beam in the beam transport line 13 by a magnetic field. As the electromagnets 25, the convergence electromagnet 19 converging the beam diameter of the charged particle beam which is being transported, and a deflection electromagnet 20 deflecting the charged particle beam are adopted. In addition, in the following, there is a case where the convergence electromagnet 19 and the deflection electromagnet 20 are described as the electromagnet 25 without distinction. Further, the plurality of electromagnets 25 are provided further toward the downstream side than at least the degrader 18 in the beam transport line 13. However, in this embodiment, the electromagnet 25 is also provided further toward the upstream side than the degrader 18. Here, as the electromagnet 25, the convergence electromagnet 19 is also provided further toward the upstream side than the degrader 18 in order to converge the beam diameter of the charged particle beam before the energy adjustment by the degrader 18. The total number of the electromagnets 25 can be flexibly changed according to the length or the like of the beam transport line 13 and is, for example, the number in a range of 10 to 40. In addition, only some of the electromagnet power sources 27 are described in FIG. 1. However, in practice, the electromagnet power sources 27 are provided in the same number as the number of electromagnets 25.

The positions of the degrader 18 and the electromagnets 25 in the beam transport line 13 are not particularly limited. However, in this embodiment, in the ESS 15, the degrader 18, the convergence electromagnet 19, and the deflection electromagnet 20 are provided. Further, in the BTS 16, the convergence electromagnet 19 is provided, and in the GTS 17, the convergence electromagnet 19 and the deflection electromagnet 20 are provided. Further, the degrader 18 is provided in the ESS 15 which is between the accelerator 11 and the rotary gantry 23, as described above, and more specifically, is provided further toward the accelerator 11 side (the upstream side) than the rotary gantry 23 in the ESS 15.

The electromagnet power source 27 supplies an electric current to the corresponding electromagnet 25, thereby generating a magnetic field of the electromagnet 25. The electromagnet power source 27 can set the strength of the magnetic field of the corresponding electromagnet 25 by adjusting an electric current which is supplied to the corresponding electromagnet 25. The electromagnet power source 27 adjusts an electric current which is supplied to the electromagnet 25 according to a signal from the control unit 30 (the details will be described later). The electromagnet power sources 27 are provided so as to correspond to the respective electromagnets 25 on a one-to-one basis. That is, the electromagnet power sources 27 are provided in the same number as the number of electromagnets 25.

The relationship between the depth of each layer of the irradiation target and an electric current which is supplied to the electromagnet 25 is as follows. That is, from the depth of each layer, the energy of the charged particle beam necessary to irradiate each layer with the charged particle beam is determined and the energy adjustment amount by the degrader 18 is determined. Here, if the energy of the charged particle beam changes, the strength of the magnetic field necessary to deflect and converge the charged particle beam also changes. Therefore, the electric current which is supplied to the electromagnet 25 is determined such that the strength of the magnetic field of the electromagnet 25 becomes strength corresponding to the energy adjustment amount by the degrader 18.

Figure 2:
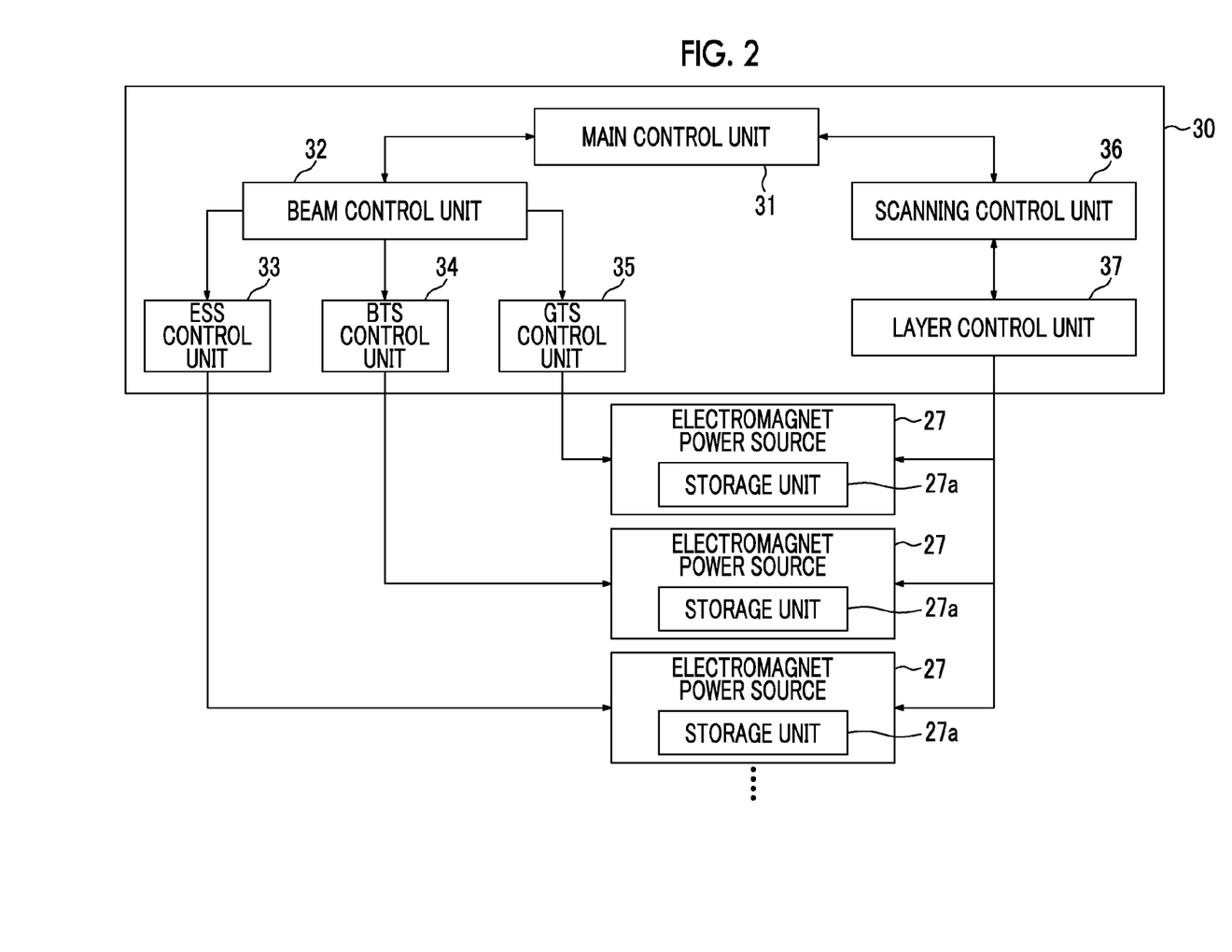
FIG. 2 is a block configuration diagram showing functions of a control unit.

Next, the details of the control unit 30 and the electromagnet power source 27 will be described with reference to FIG. 2 as well. In addition, in FIG. 2, only three electromagnet power sources 27 are described. However, in practice, corresponding electromagnet power sources 27 are provided by the number of electromagnets 25 provided in the charged particle beam irradiation apparatus 1. Further, in FIG. 2, the electromagnet 25 is not described. However, in practice, the electromagnet 25 electrically connected to the electromagnet power sources 27 is provided.

The control unit 30 controls the irradiation of the irradiation target with the charged particle beam emitted from the accelerator 11. The control unit 30 has a main control unit 31, a beam control unit 32, an ESS control unit 33, a BTS control unit 34, a GTS control unit 35, a scanning control unit 36, and a layer control unit 37.

The main control unit 31 controls the beam control unit 32 and the scanning control unit 36. Specifically, the main control unit 31 transmits a processing start signal to the beam control unit 32 and the scanning control unit 36, thereby starting processing, and transmits a processing end signal to them, thereby ending the processing.

The beam control unit 32 controls each function such that the irradiation of the irradiation target with the charged particle beam becomes possible. Specifically, the beam control unit 32 transmits a processing start signal to a cyclotron control unit (not shown) according to the processing start signal from the main control unit 31, thereby causing the accelerator 11 to perform the emission of the charged particle beam. Further, the beam control unit 32 transmits a processing start signal to the ESS control unit 33, the BTS control unit 34, and the GTS control unit 35 according to the processing start signal from the main control unit 31.

The ESS control unit 33 turns on the electromagnet power source 27 corresponding to the electromagnet 25 provided in the ESS 15 according to the processing start signal from the beam control unit 32. Similarly, the BTS control unit 34 turns on the electromagnet power source 27 corresponding to the electromagnet 25 provided in the BTS 16 according to the processing start signal from the beam control unit 32. Similarly, the GTS control unit 35 turns on the electromagnet power source 27 corresponding to the electromagnet 25 provided in the GTS 17 according to the processing start signal from the beam control unit 32. A state where it is possible to irradiate the irradiation target with the charged particle beam emitted from the accelerator 11 is created by the control of the accelerator 11 by the beam control unit 32 and the control of the electromagnet power sources 27 by the ESS control unit 33, the BTS control unit 34, and the GTS control unit 35, and thereafter, control by the scanning control unit 36 is performed.

The scanning control unit 36 controls scanning of the irradiation target with the charged particle beam. The scanning control unit 36 transmits an irradiation start signal to the scanning electromagnet 21 according to the processing start signal from the main control unit 31, thereby causing the scanning electromagnet 21 to perform irradiation to the plurality of irradiation spots on the same layer. Information about the irradiation spot in each layer is stored in the scanning control unit 36 in advance. Further, the scanning control unit 36 transmits a layer switching signal to the layer control unit 37 if the irradiation to all the spots of one layer by the scanning electromagnet 21 is completed. In the layer switching signal, information (for example, a second layer or the like) to identify a layer after switching is included.

Figure 5A:
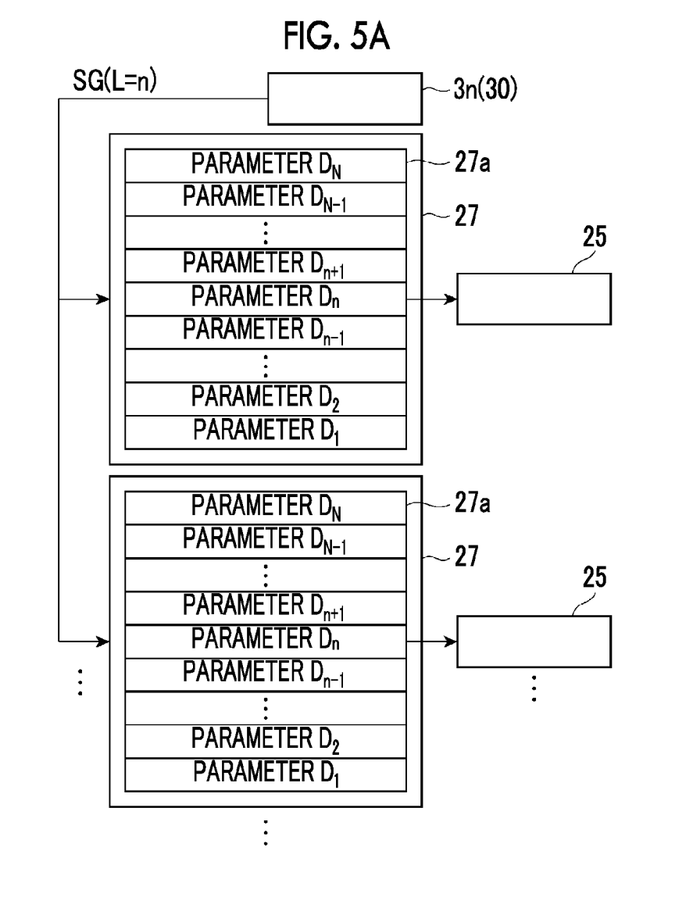
FIG. 5A is a diagram showing the parameter setting and an irradiation image of a charged particle beam.
Figure 5B:
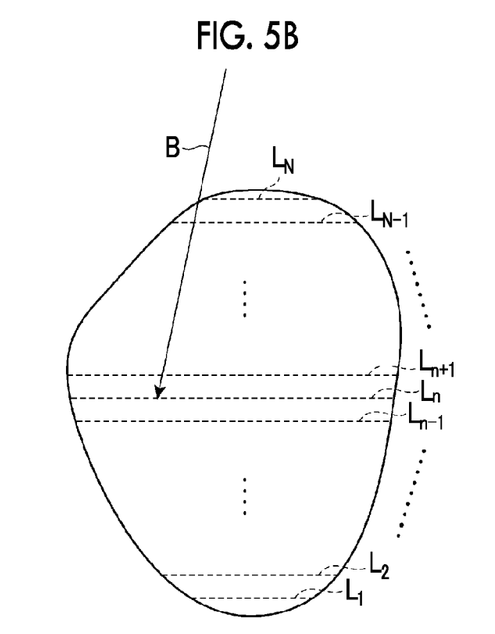
FIG. 5B is another diagram showing the parameter setting and an irradiation image of a charged particle beam.
Figure 5C:
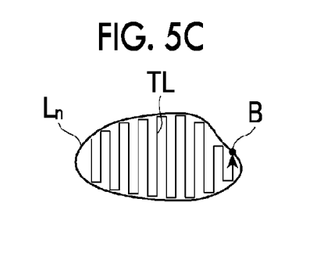
FIG. 5C is still another diagram showing the parameter setting and an irradiation image of a charged particle beam.

A charged particle beam irradiation image of the scanning electromagnet 21 according to the control of the scanning control unit 36 will be described with reference to FIGS. 5(b) and 5(c). FIG. 5(b) shows an irradiation target hypothetically sliced into a plurality of layers in a depth direction, and FIG. 5(c) shows a scanning image of the charged particle beam in one layer viewed from an irradiation direction of the charged particle beam.

As shown in FIG. 5(b), the irradiation target is hypothetically sliced into a plurality of layers in the depth direction, and in this example, the irradiation target is hypothetically sliced into N layers; a layer $L_1$, a layer $L_2$, . . . , a layer $L_{n-1}$, a layer $L_n$, a layer $L_{n+1}$, . . . , a layer $L_{N-1}$, and a layer $L_N$ in order from a deep layer (a layer in which the range of an irradiation beam B of the charged particle beam is long). Further, as shown in FIG. 5(c), the irradiation beam B is irradiated to a plurality of irradiation spots of the layer $L_n$ while drawing a beam track TL. That is, the irradiation nozzle 12 controlled by the scanning control unit 36 moves on the beam track TL.

Referring back to FIG. 2, the layer control unit 37 performs layer switching-related processing according to the layer switching signal from the scanning control unit 36. The layer switching-related processing is degrader setting processing of changing the energy adjustment amount of the degrader 18 and electromagnet setting processing of making a parameter of the electromagnet 25 a parameter corresponding to the energy adjustment amount of the degrader 18 after the degrader setting processing. The parameter of the electromagnet 25 is a target value of an electric current which is supplied to the electromagnet 25.

Here, in charged particle beam therapy, when performing the treatment of a certain patient, how to irradiate the patient with the charged particle beam is planned (a treatment plan). Treatment plan data decided at the time of the treatment plan is transmitted from a treatment planning device (not shown) to the layer control unit 37 of the control unit 30 before the treatment is performed, and is stored in the layer control unit 37. In the treatment plan data, the energy adjustment amount of the degrader 18 for irradiating each layer of the irradiation target with the charged particle beam, the parameter of the electromagnet 25 for irradiation of all the layers corresponding to the energy adjustment amount of the degrader 18, and the like are included.

The layer control unit 37 first performs the degrader setting processing as the layer switching-related processing. In the layer control unit 37, as described above, the energy adjustment amount of the degrader 18 for irradiating each layer of the irradiation target with the charged particle beam is stored in advance. Then, the layer control unit 37 sets the energy adjustment amount of the degrader 18 to a value corresponding to the layer after switching, according to the layer switching signal from the scanning control unit 36.

The layer control unit 37 performs the electromagnet setting processing after the degrader setting processing. Specifically, the layer control unit 37 transmits the layer switching signal to the respective electromagnet power sources 27 all at once, thereby making the parameters of the electromagnets 25 a value corresponding to the energy adjustment amount of the degrader 18 after the degrader setting processing. Here, the layer switching signal that the layer control unit 37 transmits to the electromagnet power sources 27 is simply a signal in which information to identify the layer after switching is included, and is not a signal in which the parameter of the electromagnet 25 corresponding to the layer after switching (the parameter of the electromagnet 25 corresponding to the energy adjustment amount of the degrader 18 after the degrader setting processing) is included. A change in the parameter of the electromagnet 25 is performed by the electromagnet power source 27. As a prerequisite thereof, the lay control unit 37 transmits the parameter of the electromagnet 25 for irradiation of all the layers corresponding to the energy adjustment amount of the degrader 18, among the treatment plan data described above, to the electromagnet power source 27 before irradiation is started (before treatment is started, rather than just before irradiation to the layer (switching)).

The electromagnet power source 27 sets the parameter of the electromagnet 25 corresponding to the layer after switching (the parameter of the electromagnet 25 corresponding to the energy adjustment amount of the degrader 18 after the degrader setting processing) according to the layer switching signal received from the layer control unit 37. Specifically, the electromagnet power source 27 has a storage unit 27a which stores the parameter of the electromagnet 25 corresponding to each layer and sets a parameter corresponding to the layer after switching, which is included in the layer switching signal, when it has received the layer switching signal from the layer control unit 37. In this way, an electric current corresponding to the layer after switching is supplied to the electromagnet 25.

Parameter setting by the electromagnet power source 27 will be described with reference to FIG. 5(a). As shown in FIG. 5(a), in all the electromagnet power sources 27, parameters $D_1$ to $D_N$ of the electromagnets 25 corresponding to the respective layers of the irradiation target, specifically, the layer $L_1$ to the layer $L_N$ (refer to FIG. 5(b)) are stored. Then, the electromagnet power source 27 sets the parameter $D_n$ according to information (L=n) to identify the layer after switching, which is included in a layer switching signal SG transmitted from the layer control unit 37.

Further, the layer control unit 37 determines that the parameter setting of the electromagnet power source 27 has been completed, after the elapse of a predetermined time (for example, in a range of 50 msec to 200 msec) after it has transmitted the layer switching signal to the electromagnet power source 27, and transmits a switching completion signal to the scanning control unit 36. Then, the scanning control unit 36 transmits an irradiation start signal to the scanning electromagnet 21 according to the switching completion signal.

Figure 3:
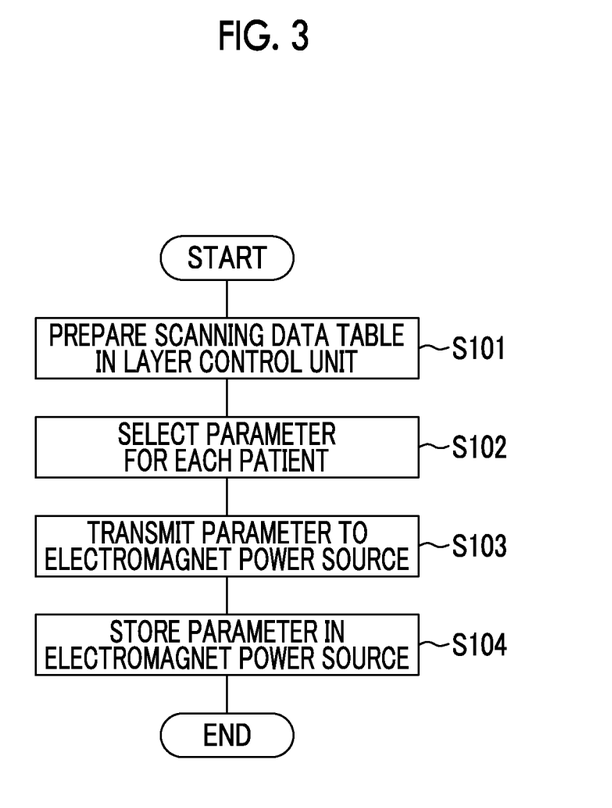
FIG. 3 is a flowchart showing the processing details of a parameter preparation step.

Next, processing of preparing (storing) the parameter of the electromagnet 25 in the storage unit 27a of the electromagnet power source 27 will be described with reference to FIG. 3.

First, a scanning data table is read from the treatment planning device by the layer control unit 37 (S101). The parameter of the electromagnet 25 for each layer is a value set in advance in consideration of the energy of the charged particle beam corresponding to the irradiation target.

Subsequently, the parameter of the electromagnet 25 is selected as transmission information to the electromagnet power source 27 by the layer control unit 37 (S102). Further, the parameter of the electromagnet 25 is managed for each layer.

Subsequently, the parameter of the electromagnet 25 is transmitted to the electromagnet power source 27 by the layer control unit 37 (S103). With respect to the parameter, the parameters of the electromagnets 25 for all the layers are put together and sequentially transmitted to the respective electromagnet power sources 27.

Finally, the parameters of the electromagnets 25 for all the layers transmitted from the layer control unit 37 are stored and memorized in the storage units 27a of the electromagnet power sources 27. The above is processing of storing the parameter of the electromagnet 25 in the storage unit 27a. If the storage processing is completed, at the time of the layer switching, the parameter setting processing of the electromagnet 25 by cooperation of the layer control unit 37 with the electromagnet power source 27 becomes possible.

Figure 4:
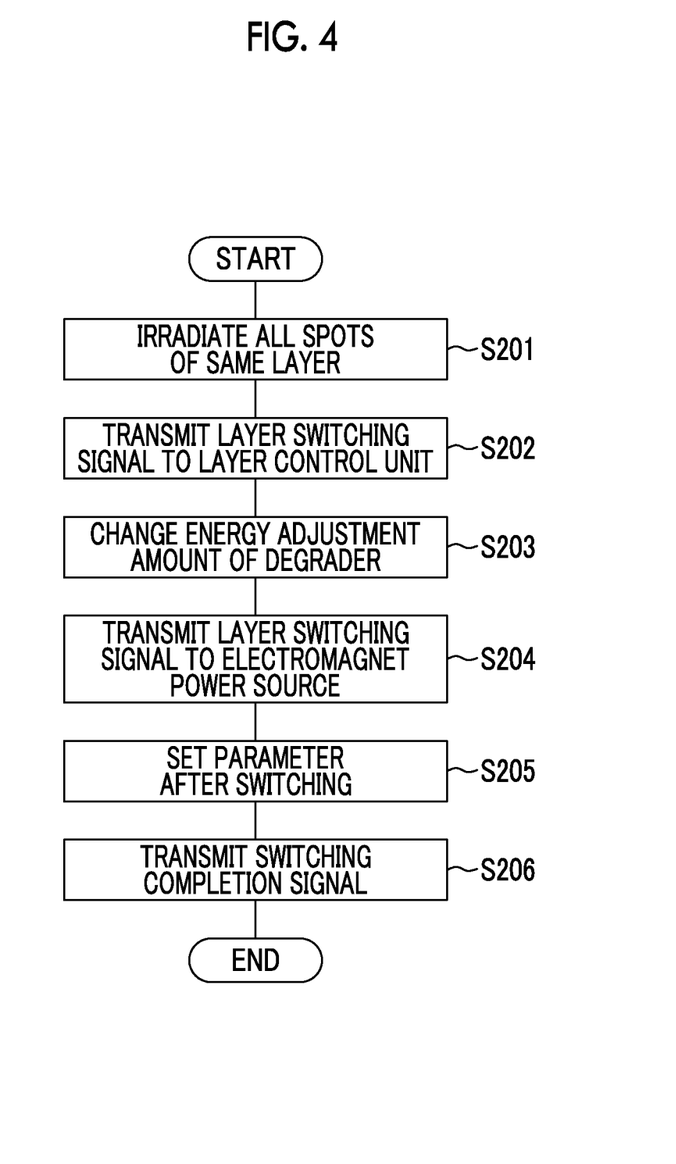
FIG. 4 is a flowchart showing the processing details at the time of layer switching.

Next, the parameter setting processing at the time of the layer switching will be described with reference to FIGS. 4 and 5. In addition, as a prerequisite to perform the processing, it is required that the parameter of the electromagnet 25 is prepared (stored) in the storage unit 27a of the electromagnet power source 27 and a state where the irradiation of the irradiation target with the charged particle beam emitted from the accelerator 11 is possible is created by the control of the accelerator 11 by the beam control unit 32 and the control of the electromagnet power source 27 by the ESS control unit 33, the BTS control unit 34, and the GTS control unit 35.

An example of irradiating the layer $L_1$ to the layer $L_N$ of the irradiation target shown in FIG. 5(b) with the charged particle beam will be described. As a prerequisite for the processing shown in the following, setting for the irradiation of the layer $L_1$ which is the deepest layer of the irradiation target with the charged particle beam is performed. Specifically, the parameter $D_1$ of the electromagnet 25 corresponding to the layer $L_1$ is set by the electromagnet power source 27.

First, all the irradiation spots of the layer $L_1$ of the irradiation target are irradiated with the charged particle beam by the scanning electromagnet 21, based on the irradiation start signal from the scanning control unit 36 (S201). If the irradiation of all the irradiation spots of the layer $L_1$ is completed, the layer switching signal SG is transmitted to the layer control unit 37 by the scanning control unit 36 (S202). In addition, in the layer switching signal SG, information (L=2) to identify the layer $L_2$ after switching is included.

Subsequently, a change in the energy adjustment amount of the degrader 18 is performed based on the layer switching signal SG from the scanning control unit 36 by the layer control unit 37 (S203). Specifically, the energy adjustment amount of the degrader 18 is changed to a value corresponding to the layer $L_2$ after switching by the layer control unit 37, based on the information (L=2) to identify the layer $L_2$ after switching, which is included in the layer switching signal SG, and the information about the energy adjustment amount of the degrader 18 for irradiation of each layer of the irradiation target with the charged particle beam, which is stored in advance.

Subsequently, the layer switching signal SG is transmitted to each electromagnet power source 27 by the layer control unit 37 (S204). In addition, the layer switching signal SG that the layer control unit 37 transmits to the electromagnet power source 27 is simply a signal in which the information (L=2) to identify the layer $L_2$ after switching is included, and is not a signal in which the parameter $D_2$ of the electromagnet 25 corresponding to the layer $L_2$ after switching (the parameter $D_2$ of the electromagnet 25 corresponding to the energy adjustment amount of the degrader 18 after the degrader setting processing) is included.

Subsequently, the parameter $D_2$ of the electromagnet 25 corresponding to the layer $L_2$ after switching (the parameter $D_2$ of the electromagnet 25 corresponding to the energy adjustment amount of the degrader 18 after the degrader setting processing) is set based on the layer switching signal SG from the layer control unit 37 by the electromagnet power source 27 (S205). In this way, an electric current corresponding to the layer $L_2$ after switching is supplied to the electromagnet 25, and thus appropriate irradiation of the layer $L_2$ after switching with the charged particle beam becomes possible.

Finally, a switching completion signal is transmitted to the scanning control unit 36 by the layer control unit 37 (S206). The above is the parameter setting processing at the time of layer switching. The scanning control unit 36 transmits the irradiation start signal to the scanning electromagnet 21 with the transmission of the switching completion signal by the layer control unit 37 as a trigger. Such processing of S201 to S206 is repeated, whereby the parameter setting processing at the time of switching to each layer is performed. That is, for example, also at the time of switching from the layer $L_{n-1}$ to the layer $L_n$, the processing of S201 to S206 described above is performed, whereby parameter setting of the layer $L_n$ after switching is performed. Then, finally, if the processing of S201 on the layer $L_N$ (the irradiation of all the spots) is completed, the irradiation completion signal indicating that the irradiation of all the layers of the irradiation target has been completed is transmitted to the main control unit 31 by the scanning control unit 36, and the radiation therapy for the corresponding patient is completed.

Next, the operation and effects of this embodiment will be described. In the charged particle beam irradiation apparatus 1 according to this embodiment, at the time of switching of a layer of the irradiation target which is irradiate with the charged particle beam, the layer switching signal in which the information to identify a layer after switching is included is transmitted from the layer control unit 37 to the electromagnet power source 27.

At the time of switching of a layer of the irradiation target in the charged particle beam irradiation apparatus, it is necessary to change the energy of the charged particle beam to energy corresponding to a layer after switching and change the parameter of the electromagnet (an electric current which is supplied to the electromagnet, or the like) so as to appropriately irradiate the layer after switching with the charged particle beam after the energy change. In the related art, at the time of switching of a layer of an irradiation target, a parameter relating to a layer after switching, of a corresponding electromagnet, is transmitted each time from a device for controlling an electromagnet power source to each electromagnet power source. The parameter of the electromagnet is a value different for each electromagnet, and a plurality of information such as an electric current which is supplied to the electromagnet is included in the parameter, and therefore, time (for example, about 1 second) is required for data communication between the device for controlling an electromagnet power source and each electromagnet power source. In this way, it takes a long time to perform layer switching.

In this regard, in the charged particle beam irradiation apparatus 1 according to this embodiment, the electromagnet power source 27 has the storage unit 27a which stores the parameter of the electromagnet 25 for each layer in the irradiation target. Then, as described above, at the time of layer switching, the layer control unit 37 transmits the layer switching signal in which the information to identify a layer after switching is included, to the electromagnet power source 27. For this reason, in the electromagnet power source 27, it is possible to set the parameter of the electromagnet 25 for the layer after switching that the storage unit 27a stores, based on the layer switching signal transmitted from the layer control unit 37. In this manner, the parameter of the electromagnet 25 for each layer is kept and stored in the storage unit 27a of the electromagnet power source 27, whereby at the time of layer switching, it is not necessary to transmit a parameter itself for each layer from the device for controlling the electromagnet power source (the layer control unit 37) to the electromagnet power source 27 and it is enough if a signal to simply give notice of a timing of switching (the layer switching signal in which the information to identify a layer after switching is included) is transmitted. Therefore, a data communication time between the layer control unit 37 and each electromagnet power source 27 can be significantly shortened (for example, 10 msec). In this way, it is possible to shorten an irradiation time by shortening a layer switching time.

Further, as described above, the information to identify a layer is included in the layer switching signal which is transmitted from the layer control unit 37 to the electromagnet power source 27. Then, the electromagnet power source 27 sets the parameter of the electromagnet 25 corresponding to the identified layer from the information to identify a layer, which is included in the layer switching signal, and the parameter of the electromagnet 25 corresponding to each layer, which the storage unit 27a stores. In this manner, the information to identify a layer is included in the layer switching signal, whereby the electromagnet power source 27 can uniquely identify the parameter of a layer which is set after switching, and thus the layer switching processing becomes easy.

Further, the irradiation nozzle 12 is mounted on the rotary gantry 23 rotatable around the irradiation target, whereby the irradiation target can be irradiated with the charged particle beam from multiple directions. In this way, it is possible to more effectively perform the irradiation of the irradiation target with the charged particle beam.

Further, the degrader 18 is provided between the accelerator 11 and the rotary gantry 23, whereby the energy of the charged particle beam emitted from the accelerator 11 can be reliably adjusted before the irradiation of the irradiation target.

Here, the degrader 18 is for receiving the charged particle beam and lowering the energy of the charged particle beam and is for emitting a gamma beam or a neutron beam by being highly activated, and therefore, in a case where the degrader 18 is disposed close to the rotary gantry 23 side (that is, the irradiation target side), there is a concern that a radiation dose in a configuration pertaining to irradiation on the irradiation target side may increase. In this regard, the degrader 18 is provided at a position closer to the accelerator 11 than the rotary gantry 23, thereby performing energy adjustment at a position sufficiently spaced apart from the irradiation target, and therefore, an increase in a radiation dose in a configuration pertaining to irradiation on the irradiation target side can be prevented.

A preferred embodiment of an aspect of the present invention has been described above. However, the present invention is not limited to the embodiment described above and may be modified within a scope which does not change the concept as set forth in each of the claims, or be applied to others.

For example, the scanning control unit 36 and the layer control unit 37 have been described as being separate configurations. However, a single configuration having the respective functions is also acceptable. Similarly, the beam control unit 32 and the scanning control unit 36 have been described as being separate configurations. However, a single configuration having the respective functions is also acceptable. Further, the layer switching signal which is transmitted from the layer control unit 37 to the electromagnet power source 27 has been described as including the information to identify a layer. However, the information to identify a layer need not necessarily be included therein, and the layer switching signal may be a signal to simply give notice of a timing of layer switching. In this case, it is necessary for an irradiation order of each layer to be stored in the storage unit of the electromagnet power source and for the parameter set by the electromagnet power source to always be managed. In this way, even if the layer switching signal is a signal to simply give notice of a timing of layer switching, it is possible to identify and set the parameter of the electromagnet corresponding to a layer after switching.

Further, a configuration is also acceptable in which fixed irradiation is performed by fixing the irradiation nozzle without using the rotary gantry 23. Further, instead of the degrader 18, another degrader may be provided at a position closer to the rotary gantry than the cyclotron.

According to an aspect of the present invention, it is possible to provide a charged particle beam irradiation apparatus in which it is possible to shorten an irradiation time by shortening a layer switching time.

It should be understood that the invention is not limited to the above-described embodiment and may be modified into various forms on the basis of the spirit of the invention. Additionally, the modifications are included in the scope of the invention.

What is claimed is:

1. A charged particle beam irradiation apparatus comprising: an accelerator which accelerates charged particles and emits a charged particle beam;
   an irradiation unit which irradiates an irradiation target with the charged particle beam;
   a transport line which transports the charged particle beam emitted from the accelerator, to the irradiation unit;
   an energy adjustment unit which is provided at the transport line and adjusts energy of the charged particle beam;
   a plurality of electromagnets provided further toward the downstream side than the energy adjustment unit in the transport line;
   an electromagnet power source provided to correspond to each of the plurality of electromagnets; and
   a control unit which controls a parameter of each electromagnet according to the energy of the charged particle beam,
   wherein the electromagnet power source has a storage unit which stores the parameter of each electromagnet for each layer which is irradiated with the charged particle beam, in the irradiation target, and
   the control unit transmits a signal relating to switching of the layer to each electromagnet power source.

2. The charged particle beam irradiation apparatus according to claim 1, wherein the control unit transmits a signal to identify the layer, as the signal relating to switching of the layer, and
   each electromagnet power source sets a parameter of one layer among the parameters of the electromagnet stored for each layer, according to the signal to identify the layer received from the control unit.

3. The charged particle beam irradiation apparatus according to claim 1, further comprising:

a rotary gantry rotatable around the irradiation target, wherein the irradiation unit is mounted on the rotary gantry, and the energy adjustment unit is provided between the accelerator and the rotary gantry.

4. The charged particle beam irradiation apparatus according to claim 3, wherein the energy adjustment unit is provided at a position closer to the accelerator than the rotary gantry.

* * * * *